United States Patent [19]

Ackermann et al.

[11] 3,969,344

[45] July 13, 1976

[54] METHOD OF PURIFYING POLYMERIZABLE ORGANIC SUBSTANCES

[75] Inventors: Jacob Ackermann, Varese; Pierino Radici, Como, both of Italy

[73] Assignee: Societa' Italiana Resine S.p.A., Milan, Italy

[22] Filed: Nov. 4, 1971

[21] Appl. No.: 195,840

[30] Foreign Application Priority Data

Nov. 12, 1970 Italy.................................. 31632/70

[52] U.S. Cl....................... 260/239.3 A; 260/343.5; 260/343.6; 260/343.9; 260/677 A; 260/677 AD; 260/669 A; 260/654 S; 260/318; 260/345.9; 260/340; 260/340.9; 260/343; 260/708; 210/38 R; 260/340.6; 260/346.1 R; 260/348 R; 260/293.86; 260/326.5 FN; 260/561 N; 260/465.9; 260/601 R

[51] Int. Cl.²........................................ C07D 201/16

[58] Field of Search.................. 260/239.3 A, 340.7, 260/340.9, 343, 708, 340; 210/38

[56] References Cited

UNITED STATES PATENTS

| | | | |
|---|---|---|---|
| 2,622,097 | 12/1952 | Osborne........................... | 260/465.9 |
| 2,692,878 | 10/1954 | Kahr............................ | 260/239.3 A |
| 2,828,307 | 3/1958 | Soeterbroek et al. ....... | 260/239.3 A |

OTHER PUBLICATIONS

"Ion Exchangers in Organic and Biochemistry" Edited by Calmon and Kressman (Interscience) (1957), Chapter 15 by H. F. Walton, pp. 640–657.

*Primary Examiner*—Henry R. Jiles
*Assistant Examiner*—Robert T. Bond
*Attorney, Agent, or Firm*—Sughrue, Rothwell, Mion, Zinn & Macpeak

[57] ABSTRACT

A process for purifying a polymerisable monomer selected from the group consisting of cyclic ethers, hydrocarbon olefins, vinyl compounds, aldehydes, lactams of the formula:

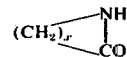

wherein $x$ is an integer from 3 to 13 and lactones of the formula:

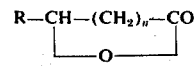

wherein $n$ is an integer of from 1 to 4 and wherein R represents an hydrogen atom, an alkyl group or an aryl group; said process comprising contacting a liquid consisting of said monomer at a temperature of not greater than 130° centigrade and at a pressure sufficient to keep said monomer in liquid form, with a solid absorbent consisting essentially of a porous reticulated macromolecular alkali metal or alkaline earth metal salt of a cationic exchange resin containing carboxylic, sulfonic or phosphoric acid groups, said cationic exchange resin having a specific surface area of at least one square meter per gram and a pore diameter of from $10^{1.3}$ to $10^5$ angstroms and recovering the purified monomer.

11 Claims, No Drawings

METHOD OF PURIFYING POLYMERIZABLE ORGANIC SUBSTANCES

The present invention relates to a process for purifying polymerizable organic substances, more particularly it relates to obtaining in extremely pure form those organic substances which, in the industry, are intended for the production of polymers of high molecular weight.

A high degree of purity in substances which are subjected to polymerization is necessary insofar as it permits the preparation of polymers of high molecular weight, a high reactivity of the polymerization system, a high yield of polymer and a low consumption of catalyst.

The nature of extraneous organic substances present in the polymerizable organic monomers or organic substances obviously varies according to the monomer and its origin. In addition, the action of such impurities in polymerization varies, at least to a certain extent, according to the type of polymerization to which the monomers are subjected.

Thus, for example, in a polymerization of the ionic type, the impurities which act on the reagent system are of a polar nature. Impurities, such as for example water, alcohols and carboxylic acids, can act on the catalytic system as inhibitors or as chain transferers.

The effect of chain transference is known not only on the molecular weight of the polymers but also on the nature of the terminal groups of the macromolecular chains.

Thus, for example, in the cationic polymerization of trioxane, chain transferers having the characteristics of proton donors greatly encourage the formation of hemiacetal terminal groups which are terminally unstable.

The industry has therefore felt the need to have at its disposal monomers of the highest possible purity, for subjection to polymerization, also in consideration of the influence of various impurities on the characteristics of the polymers.

For all the reasons described, various techniques have been suggested for purifying monomers, such as fractional or extractive distillation, crystallization and zone-wise fusion, extraction and treatments with compounds which react to some impurities in the monomers.

Such methods almost always prove disadvantageous by reason of their high economic cost and because in the difficulty of achieving the desired degree of purity. In fact, difficulties are often encountered which depend upon the actual reactivity of the purified monomers, in fact by their nature of reactive substances, they tend to give rise to secondary reactions.

Another method used for simplicity, economy and speed is that which employs selective absorbents. This method, however, has various drawbacks.

In fact, the hitherto used absorbents, such as for example silica gel, alumina, aluminium silicates, diatomaceous earths and active carbon, are generally effective, but their effect is limited to a single impurity contained in the treated substance.

Furthermore, due to the very reactivity of the monomers, polymerization phenomena may occur during purification.

Finally, the known absorbents may catalyze reactions which transform traces of monomers into other undesired compounds, particularly when purification is carried out at elevated temperatures.

For all these reasons, the use of solid absorbents of the prior art has been rather limited, also in consideration of their excessive fragility under the conditions in which polymerizable organic monomers are purified.

SUMMARY OF THE INVENTION

It has now been found that the drawbacks of the prior art can be avoided or at least substantially reduced, by the process of the present invention which consists essentially in bringing the polymerizable organic monomers, in liquid form, in contact with a solid absorbent constituted by substances of a polymeric nature containing carboxyl, sulphonic or phosphoric groups in salified form.

Therefore, the object of the present invention consists in a process for obtaining polymerizable organic monomers in pure form and in a particular class of solid absorbents suitable for such purification.

More particularly, the absorbents of the present invention consist of a porous matrix, with a specific surface area of at least 1 sq.m./gr, constituted by a preferably reticulated macromolecular organic substance, or a substance which is insoluble in the monomer which is subjected to purification, the carboxyl, sulphonic or phosphoric groups being bonded to the said matrix in the form of salts of alkali metals or alkaline earth metals.

It has been found that by working according to the process of the present invention, pure monomers are obtained and undesired secondary reactions are avoided when the macromolecular matrix has a porous structure with pores of a diameter between $10^{1.3}$ to $10^5$ Angstrom units.

Although any substances of a polymeric nature having salified acid groups and having the characteristic features which have been defined hereinabove are useful for the purpose, in the preferred embodiment of the present invention, solid absorbents are used which consist of ionic, cationic and macromolecular exchange resins, which have been previously treated in order to convert the acid groups to salts of alkali metals or alkaline earth metals.

Cationic and ionic exchange resins are for example those described by F. Helfferich in "Ion Exchange", on pages 29 et seq. The absorbents preferably used in the present invention are salts of alkali metals or alkaline earth metals for ionic exchange resins based on carboxylated polyphenol (polyacrylic) or sulphonated polyphenol or polystyrene, those absorbents being particularly preferred which have a matrix constituted by the product of copolymerization in styrene beads with a divinyl monomer such as divinyl benzene.

According to the process of the present invention, the polymerizable organic monomers, in liquid form, are brought into contact with the previously defined absorbents at a temperature equal to or less than 130°C.

Working above this temperature in fact normally produces a substantial reduction in the absorption capacity. It has been found that a wide variety of organic substances can be purified according to the process of the present invention, and particularly advantageous results are obtained in the purification of monomers belonging to the following classes:

cyclic ethers such as for example trioxane, tetraoxane, dioxolane tetrahydrofurane, 3,3-bis (chloromethyl)-oxyethane;
lactams having the following general formula:

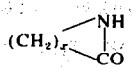

in which $x$ assumes values comprised between 3 and 13;
lactones having the following general formula:

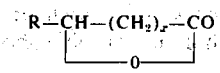

in which $x$ assumes values comprised between 1 to 4 and R represents hydrogen or an alkyl or aryl radical;
olefins, such as for example isobutylene, propene or ethylene;
vinyl compounds such as for example styrene, alphamethylstyrene, vinyl carbazol, acrylamide, acrylonitrile and vinyl chloride;
aldehydes such as for example acroleine, methacroleine and 5,6-dihydro - 1,2 - pyran - 3 - carboxaldehyde.

According to the process of the present invention, purification is carried out at the lowest possible temperature, but in any case at a temperature equal to or greater than the melting temperature of the monomer which is being subjected to treatment. When working with liquid monomers, a temperature below boiling temperature is maintained.

In addition, the pressure used in the purification of monomers is not critical, but it is nevertheless preferable to work at atmospheric pressure or at a pressure above atmospheric pressure, particularly in the treatment of monomers which are gaseous at ambient pressures under the conditions of temperature in which purification is carried out.

According to the process of the present invention, impure liquid monomers are brought into contact with the solid absorbent under conditions of temperature and pressure as previously defined.

For this purpose, any known technique may be used to establish contact between liquid products and solid products.

Thus, for example, it is possible to blend the monomers with the absorbent and then separate the liquid products from the solids. However, in the preferred form, the monomers are fed continuously to the end of a reactor of elongated form containing the absorbent as a fixed bed, and the purified product is recovered at the other end of the reactor. The capacity of the absorbent, in other words the quantity of purified product which can be obtained per unit of absorbent by weight, depends on the quantity of impurities contained in the monomer which is subjected to purification, as well as on the particular nature of such impurities.

In any case, regeneration of the exhausted absorbent takes place by disabsorption of the impurities.

Such disabsorption may be carried out by various methods which may consist in disabsorption at below ambient pressure, or by using a scavenging gas at elevated temperature and preferably above absorption temperature.

For example, temperatures equal to or greater than 150°C may be used, but they must in any case be below those at which the absorbent is decomposed.

Another regeneration technique consists in washing with a solvent which is capable of disabsorbing the impurities, followed by elimination of the actual solvent.

Finally, according to a preferred method, the exhausted absorbent is first treated with an inert solvent in order to recover the residual monomer, this stage being followed by disabsorption of the impurities by using an inert gas at elevated temperature.

By working according to the process of the present invention, the impurities contained in the polymerizable organic monomers are virtually completely eliminated, without giving rise to any undesired secondary reactions such as for example polymerizations or transformations to other compounds.

As will be obvious from the experimental examples, the purified monomers can be transformed into polymers of high molecular weight at high rates of polymerization and with a low consumption of polymerization catalyst.

A low consumption of catalyst in polymerization, beyond being economically advantageous, makes it possible to obtain polymers with a greater degree of purity.

It is in fact well-known that catalytic residues result in the most part in harmful cases, in that they give rise to degradative processes during subsequent transformation of the polymer. By polymerizing the purified monomers according to the process of the present invention, by virtue of the small quantity of catalyst, it is possible to avoid elimination of the catalytic residue from the polymer or at least any such elimination is far more easily performed.

EXAMPLE 1

A sample of pure commercial trioxane is purified by percolation in the molten state through a macroreticular exchanger column, known commercially as Amberlite 200, with sulphonic groups salified in the form of a sodium salt. The exchanger resin is placed in a glass column with an inside diameter of 2.5 cm and measuring 1 meter in height, fitted with an outer sleeve for thermostatic control by circulating air. The height of the resin bed equals 80 cm.

The salified resin, after it has been charged into the column, is brought to the temperature of 160°C while anhydrous nitrogen is passed through the column from the bottom at a speed of 150 to 180 l/hr. In this way, the resin is rendered anhydrous to the point of having a residual moisture content below 0.1% by weight, determined by the Karl-Fischer method.

The temperature is then brought to 65°C and commercial trioxane is percolated through the resin at the rate of 450 to 500 ml/hr, while a stream of anhydrous nitrogen is kept washing over the top of the column.

After having percolated a quantity of trioxane equal to 100 kg per kg of resin, the product discharged still has a water content of less than 10 ppm, as determined by the Karl-Fischer method.

This content is determined on samples of 50 g of molten trioxane drawn off by preheated and perfectly dried pipette.

100 g of trioxane purified in this way are introduced directly in the molten state into a steel reactor. The form of this reactor is such that the final solid polymer is in the form of an easily extractable sheet. The reactor is also provided with an agitator and a sleeve for measurement of the temperature by a thermocouple, and it is fitted with two apertures in the top, one for introduction of the monomer and one for maintaining an inert atmosphere by means of a stream of nitrogen.

The reactor is immersed in a heated oil bath so as to maintain an internal temperature equal to 65°C.

Using a microsyringe, 0.0045 g of boron trifluoride is added to the reactor in the form of boron trifluoride diethyl etherate, in a 1% solution in nitrobenzene, and the agitator is run for 10 seconds.

After one minute, the reaction commences with formation of a polymer which is insoluble in trioxane and after a few seconds the polymer takes the form of a solid block. After 5 minutes, polymerization is stopped by cooling to 0°C.

The polymer, converted to powder, is treated with a 1% methanol solution of triethanol amine at boiling for 30 mins in order to eliminate residue of catalyst and monomer.

The polymer, filtered and washed thoroughly with methanol, is dried in an oven at 70°C and at a pressure below atmospheric pressure.

The yield of polymer and the inherent viscosity thereof are then determined. This latter value is determined at 60°C in a solution of parachlorophenol containing 2% alpha-pinene with a concentration of polymer equal to 0.5 g for every 100 ml of solvent.

The results are set out in Table 1.

In particular, the table shows as $T_1$ the time in minutes which elapses between introduction of the catalyst and commencement of formation of the trioxane-insoluble polymer, while $T_2$ indicates the total polymerization time in minutes, R represents the ratio of $T_2/T_1$, while $\eta$ in represents the inherent viscosity.

EXAMPLE 2

By way of comparison, the commercial trioxane of the first example is subjected to a process of purification by a conventional technique.

500 g trioxane are treated with 15 g potassium under reflux for 6 hours in a one-liter flask with a rotary evaporator. In the reflux condenser, a pump maintains circulation of water which is thermostatically controlled to a temperature of 62°C to prevent crystallization of the trioxane on the condenser. A stream of nitrogen washing over the top of the condenser ensures anhydrous conditions in the system.

At the end of the process, the valve of the rotary evaporator is opened and the trioxane is rapidly distilled at a pressure a little below atmospheric.

100 g of the trioxane which has been thus purified are introduced in the molten state into the reactor described in the first example and a similar procedure is followed to that in the first example, 0.0045 g boron trifluoride being added in the form of boron trifluoride diethyl etherate in a 1% solution in nitrobenzene.

The agitator is then operated for 10 seconds. After 2 minutes, reaction commences with the formation of the polymer in the liquid trioxane and after a few seconds a block of polymer forms.

After 10 minutes, the reaction is stopped and the test described in the first example is performed.

The results are summarized in Table 1.

Table 1

| Example | $T_1$ | $T_2$ | R | Yield (gr) | $\eta$ in. |
|---------|-------|-------|---|------------|------------|
| 1 | 1 | 5 | 5 | 73 | 2.41 |
| 2 | 2 | 10 | 5 | 48 | 1.08 |

EXAMPLE 3

A sample of pure commercial trioxane is purified by percolation in the molten state through a column of macroreticular cationic exchange resin known under the trade name of Amberlyst-15, having sulphonic groups salified with calcium.

The operation is carried out by the method described in the first example.

100 g purified trioxane are introduced into the reactor described in the first example, an atmosphere of nitrogen being maintained at a temperature of 60°C; 1.5 g $CH_3-O(CH_2-O)_2-CH_3$ and then 0.0035 g boron trifluoride in the form of boron trifluoride diethyletherate in 1% nitrobenzene are introduced into the reactor.

The agitator is operated for 10 seconds. After 30 seconds, the reaction commences with formation of a polymer which is insoluble in trioxane. After 2 minutes, the reaction is stopped by cooling.

The block of polymer is extracted from the reactor and subjected to the treatments described in the first example.

A sample of the polymer is subjected to thermal degradation in a nitrogen atmosphere at 220°C in order to determine the fraction of polymer, the macromolecular chains of which are blocked by $O-CH_3$ groups.

Indicated as the thermally stable part is the percentage of residual polymer after 60 minutes of such treatment.

This value is shown by $K_s$ in Table 2.

The inherent viscosity of the part of the polymer remaining after thermal degradation treatment is then determined.

This value is indicated as $\eta$ in $(K_s)$ in Table 2. The other figures set out in the table have the same significance as in the first example.

EXAMPLE 4

By way of comparison, the trioxane purified as described in Example 2 is subjected to polymerization under the conditions described in Example 3.

100 g of this trioxane are introduced into the reactor described in Example 1, a nitrogen atmosphere and a temperature of 70°C being maintained.

1.5 g $CH_3-O-(CH_2-O)_2-CH_3$ and then 0.0035 g boron trifluoride in the form of boron trifluoride diethyletherate in 1% solution in nitrobenzene are then introduced into the reactor. The agitator is operated for 10 seconds.

After 2 minutes, formation of the polymer commences; after 8 mins, the polymerization reaction is stopped by cooling to 0°C.

The polymer is extracted from the reactor and subjected to the tests described in Example 3. The results are set out in Table 2.

EXAMPLE 5

A sample of 700 g of crude 1,3-dioxolane, obtained by the reaction of formaldehyde, in a 37% aqueous solution, and ethylene oxide, using boron trifluoride as a catalyst, contains after first adjustment of the reaction product: 6.2% water, 0.5% methanol, acid products and particularly formic acid 0.2% by weight.

Further purification of the mixture is laborious and difficult due to the formation of water-dioxolane azeotrope, and due to the closeness of the boiling point of methanol to that of the dioxolane.

The crude dioxolane is percolated through a column of macroreticular cationic exchange resin known commercially as Amberlite 200 in which the sulphonic groups take the form of potassium salts.

The apparatus is identical to that described in the first example and the height of the resin bed is 70 cm.

Prior to percolation, the resin is rendered anhydrous by the same methods as described in the first example.

The dioxolane is percolated through the resin at ambient temperature and at a speed of 450 to 470 ml/hr.

A nitrogen atmosphere is maintained during percolation.

Upon gas chromatographic analysis, the purified dioxolane contains 22 ppm of water, 28 ppm of methanol and less than 20 ppm of formic acid.

EXAMPLE 6

A sample of 3 kg commercial caprolactam is percolated in the molten state through a column of macroreticular cationic exchanger resin of the type used in Example 1, having sulphonic groups salified with potassium. A similar procedure is adopted to that in Example 1, the temperature being maintained at 80°C by circulation of oil through the outer jacket. The rate of supply of caprolactam equals 350 to 370 ml/hr and an inert gas ambient is maintained.

A sample of 100 g of caprolactam purified in this way is converted to the molten state and transferred by a hot and perfectly dried pipette to a glass reactor which is in the form of a test tube.

The tube, which has an inside diameter of 1.5 cm and a height of 15 cm, is fitted with a capillary extending to 0.5 to 1 cm from the bottom, which is used for introduction of a continuous stream of anhydrous nitrogen.

The small hole in the cover of the tube constitutes a vent.

To the caprolactam maintained at 90°C is added 0.003 g sodium, in the form of a 50% dispersion in paraffin. The mixture is then brought to a temperature of 260°C in an oil bath while nitrogen is passed continuously through the capillary. The progress of polymerization is followed by the stream of nitrogen emerging from the capillary.

When polymerization commences, the rate of passage of the gas diminishes until it stops altogether.

The reaction of polymerization commences after approx. 1.5 minutes of the mixture being at 260°C.

After a total period of 6 minutes, polymerization is stopped by cooling to 20°C.

The product of reaction obtained is ground and dissolved, under agitation, in 100 ml 90% formic acid at a temperature of 25°C.

The polymer is then obtained by precipitation, by the addition of water (200 ml) to the solution which is agitated by a turbine agitator. The polymer is filtered and washed thoroughly with water until the washing liquors give a neutral reaction when tested with a litmus paper.

The product is finally dried in an oven at 70°C at a pressure below ambient pressure.

The yield of polymerization and the inherent viscosity of the polymer are then determined.

The inherent viscosity ($\eta$ in) is determined in 99% formic acid at 25°C with a concentration of 0.5 g polymer to 100 ml of solvent.

The results are set out in Table 3.

Table 2

| Example | $T_1$ | $T_2$ | R | Yield (gr) | $\eta$ in | $K_s$ | $\eta$ in($K_s$) |
|---------|-------|-------|---|------------|-----------|-------|------------------|
| 3       | 0.5   | 2     | 4 | 80.2       | 1.60      | 83    | 1.58             |
| 4       | 2     | 8     | 4 | 55         | 0.50      | 81    | 0.48             |

EXAMPLE 7

For purposes of comparison, commercial caprolactam of the type used in Example 6 is subjected to purification. 100 g of this caprolactam are dissolved in 350 ml anhydrous toluene in a 500 ml 3-neck flask fitted with an agitator and also with a collector with a capacity of 20 ml, with a tap, surmounted by a reflux cooler of the type used for determining water with a light solvent (Dean and Stark apparatus).

The system is maintained under anhydrous conditions by a stream of nitrogen washing over the top of the cooler.

The mixture is heated in an oil bath and maintained at boiling for about 20 hours. In this way, the water is extracted through the azeotrope with toluene, the azeotropic mixture is collected in the collector and discharged through the tap.

80 ml of liquid are discharged in this way.

After cooling, the collector is replaced and the reflux cooler is provided with a Liebig refrigerant and a 2-neck 500 ml collecting flask is fitted. A stream of nitrogen washes over one mouth of the collecting flask in order to exclude the possibility of humidity absorption.

The solution is heated and the toluene eliminated by distillation and atmospheric pressure.

The final traces of toluene are eliminated by working at a pressure of approx. 100 mmHg with an oil bath temperature of 90°/100°C and in a nitrogen atmosphere.

The caprolactam is then distilled at a pressure of 0.05 to 0.03 mmHg and a temperature of 93° to 95°C.

10 g of distilled caprolactam are subjected to polymerization under the conditions described in Example 6.

The product of polymerization is analysed after 6 minutes and after 1 hour of being maintained at 260°C.

The results are set out in Table 3.

This table shows the values for concentration of sodium, used as the catalyst, expressed as a percentage by weight, the duration of polymerization in minutes, the conversion of caprolactam as a percentage by weight with respect to the charge and the inherent viscosity of the polymer.

Table 3

| Example | % sodium | Polymerization time | Conversion | $\eta$ in |
|---------|----------|---------------------|------------|-----------|
| 6       | 0.03     | 6                   | 81.4       | 3.42      |
| 7       | 0.03     | 6                   | 1          | —         |
|         | 0.03     | 60                  | 5.5        | 0.28      |

EXAMPLE 8

A sample of 10 g of caprolactam purified as described in Example 6, has added to it 0.004 g metallic sodium in the form of a 50% dispersion in paraffin.

The operations and methods of polymerization are still those described in Example 6.

The reaction commences after approx. 1½ mins. from the moment the system is brought to 260°C. After a total time of 6 minutes, polymerization is stopped by cooling to 20°C. The product is treated and analysed as described in Example 6.

The results are summarized in Table 4.

EXAMPLE 9

By way of comparison, the caprolactam purified as described in Example 7 is polymerized by the addition of sodium in a quantity equal to 0.004 g per 10 g of caprolactam.

Polymerization proceeding as described in Example 6, reaction commences after approx. 10 minutes from the system being brought to 260°C.

The products of polymerization are analyzed after 6 minutes and 18 minutes from commencement of polymerization. The results are set out in Table 4.

Table 4

| Example | % sodium | polymerization time | conversion | $\eta$ in |
|---------|----------|---------------------|------------|-----------|
| 8 | 0.03 | 6 | 83 | 3.26 |
| 9 | 0.03 | 6 | 3 | — |
|   | 0.03 | 18 | 35.5 | 1.16 |

EXAMPLE 10

A sample of 2.5 g pure commercial ε-caprolactone containing 0.552% water, determined by the Karl Fischer method, is purified by percolation through a column of macroreticular cationic exchanger resin known commercially as Amberlyst 15, having sulphonic groups salified with lithium. The apparatus and the method used are those described in the first example.

The height of the resin bed is equal to 70 cm, the temperature is maintained at 60°C and the rate of percolation is regulated at approx. 800 ml/hr.

After purification, the caprolactone has a water content below 10 ppm, being determined by the Karl Fischer method.

EXAMPLE 11

A sample of 500 g commercial ε-caprolactone of the type described in Example 10 is placed in a 1-liter vessel and 30 g anhydrous sodium sulphate added.

The vessel is placed in a refrigerator for approximately 20 hours at a temperature of 0° to approx. 5°C.

The caprolactone is then filtered directly under nitrogen in a rotating evaporator, and distilled under a vacuum at 0.05 to 0.03 mmHg with a bath temperature of 83° to 85°C.

The humidity is determined by the Karl Fischer method on 50 g of the distilled product. The sample has a humidity content equal to 107 ppm.

EXAMPLE 12

A sample of 500 g caprolactone purified as described in Example 11 is treated under agitation in a 1-liter flask with 10 g toluenediisocyanate and then it is distilled.

The operation is carried out as described in *Makromoleculare Chemie* 56 (1963) 179.

The caprolactone which is thus treated has a water content equal to 57 ppm, determined by the Karl Fischer method.

We claim:

1. A process for purifying a polymerizable monomer selected from the group consisting of trioxane, 1,3-dioxolane, caprolactone and caprolactam by removing impurities in the form of water, alcohols and carboxylic acids; said process consisting of contacting a liquid consisting only of said monomer in liquid form at a temperature of not greater than 130° centigrade and at a pressure sufficient to keep said monomer in liquid form with a solid absorbent consisting essentially of a porous reticulated macromolecular alkali metal or alkaline earth metal salt of a cationic exchange resin containing carboxylic, sulfonic or phosphoric acid groups, said cationic exchange resin having a specific surface area of at least one square meter per gram and a pore diameter of from $10^{1.3}$ to $10^5$ angstroms and recovering the purified monomer.

2. The process of claim 1, wherein said solid absorbent consists essentially of a porous reticulated macromolecular alkali metal or alkaline earth metal salt of a cationic exchange resin selected from the group consisting of carboxylated polyphenol resins, sulphonated polyphenol resins, and sulphonated polystyrene resins.

3. The process of claim 1, wherein said solid absorbent consists essentially of a porous reticulated macromolecular alkali metal or alkaline earth metal salt of a cationic exchange resin consisting essentially of a copolymer of styrene with a divinyl monomer.

4. The process of claim 3, wherein said divinyl monomer is divinyl benzene.

5. The process of claim 1, wherein said contacting is conducted at a temperature at least equal to the melting point of said polymerizable monomer but not greater than the boiling point thereof.

6. The process of claim 5, wherein said contacting is conducted by passing said monomer through a fixed bed of said solid absorbent.

7. The process of claim 5, wherein said solid absorbent is regenerated after said contacting by first treating with an inert solvent to recover residual monomer and thereafter removing the absorbed impurities therefrom by contacting the solid absorbent at a temperature of at least 150°C but not greater than the decomposition point of said absorbent with an inert gas.

8. The process of claim 5, wherein said monomer is trioxane.

9. The process of claim 5, wherein said monomer is 1,3-dioxolane.

10. The process of claim 5, wherein said monomer is caprolactam.

11. The process of claim 5, wherein said monomer is ε-caprolactone.

* * * * *